United States Patent [19]
Graef

[11] Patent Number: 5,059,057
[45] Date of Patent: Oct. 22, 1991

[54] HIGH STRENGTH, THIN-WALLED, PLASTIC TUBES AND CONNECTOR COMBINATION AND METHOD OF FABRICATION

[76] Inventor: Andrew Graef, 731 N. Marengo, Pasadena, Calif. 91103

[21] Appl. No.: 593,098

[22] Filed: Oct. 5, 1990

[51] Int. Cl.⁵ .............................................. F16B 7/00
[52] U.S. Cl. .................................... 403/298; 403/292
[58] Field of Search ................ 403/292, 298; 52/726, 52/586, 731

[56] References Cited

U.S. PATENT DOCUMENTS 3,786,612  1/1974  Baker ................................. 403/295
4,678,148  7/1987  Winn ............................. 403/292 X

FOREIGN PATENT DOCUMENTS 1522724  8/1978  United Kingdom ................ 403/295

*Primary Examiner*—Andrew V. Kundrat
*Attorney, Agent, or Firm*—Beehler & Pavitt

[57] ABSTRACT

A high strength plastic tube and connector combination wherein the plastic material is short carbon-fiber resin, such as polyetheretherketone (PEEK), which is extruded to form the tube with an axially extending matrix of internal support walls to form a plurality of passageways; and the connector is formed by injection molding with a short cylindrical section having a similar matrix of reinforcing walls, but with axially ending projections from its end or ends, which projections are shaped to fit slideably into the passageways at the end of the tube, to be secured therein by a structural aircraft adhesive.

11 Claims, 2 Drawing Sheets

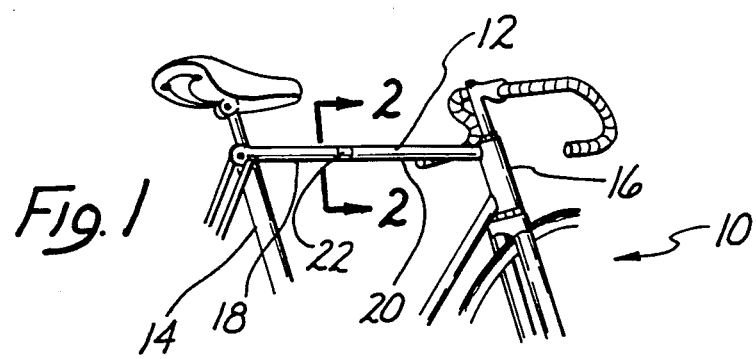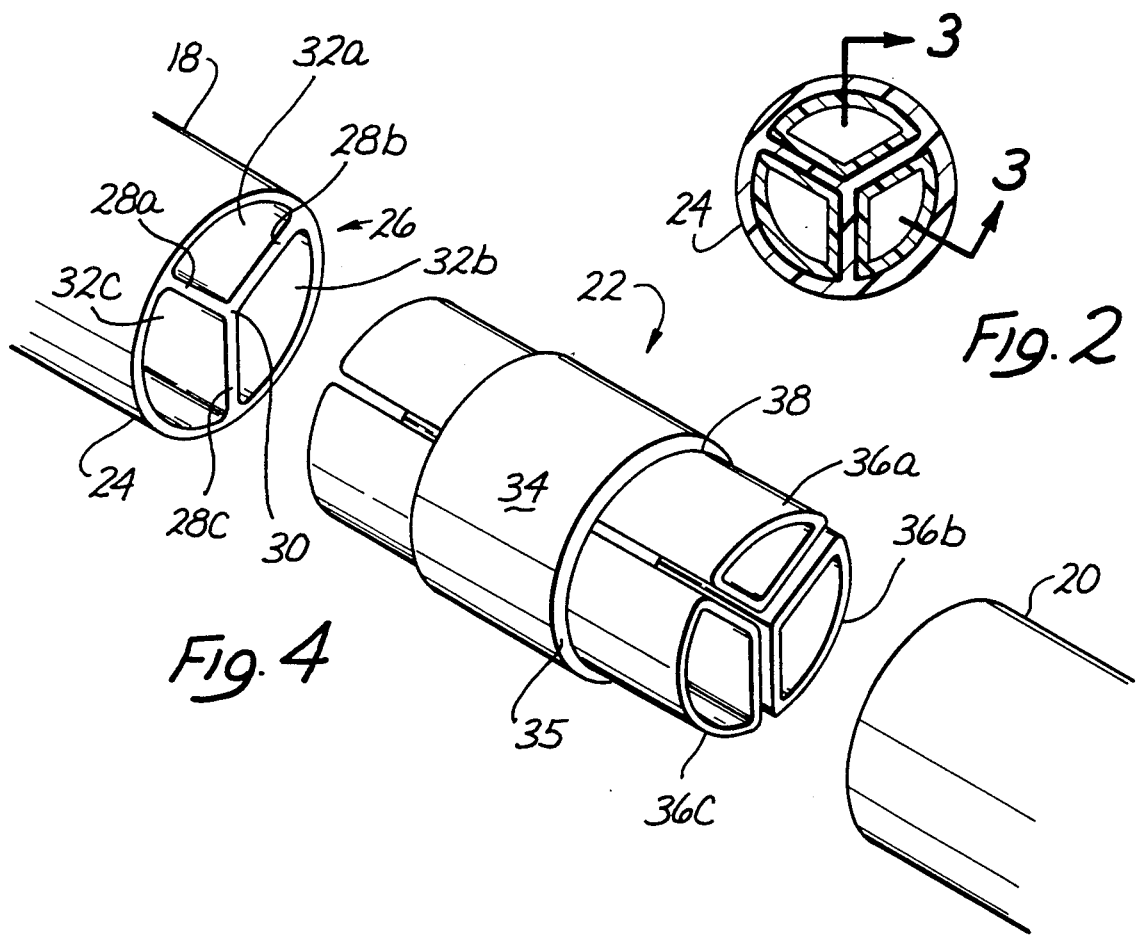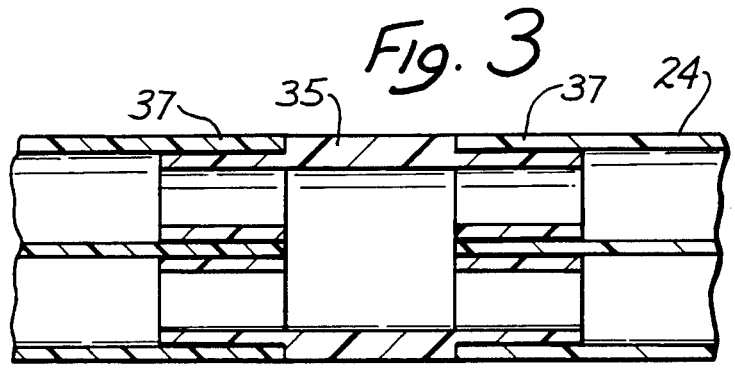

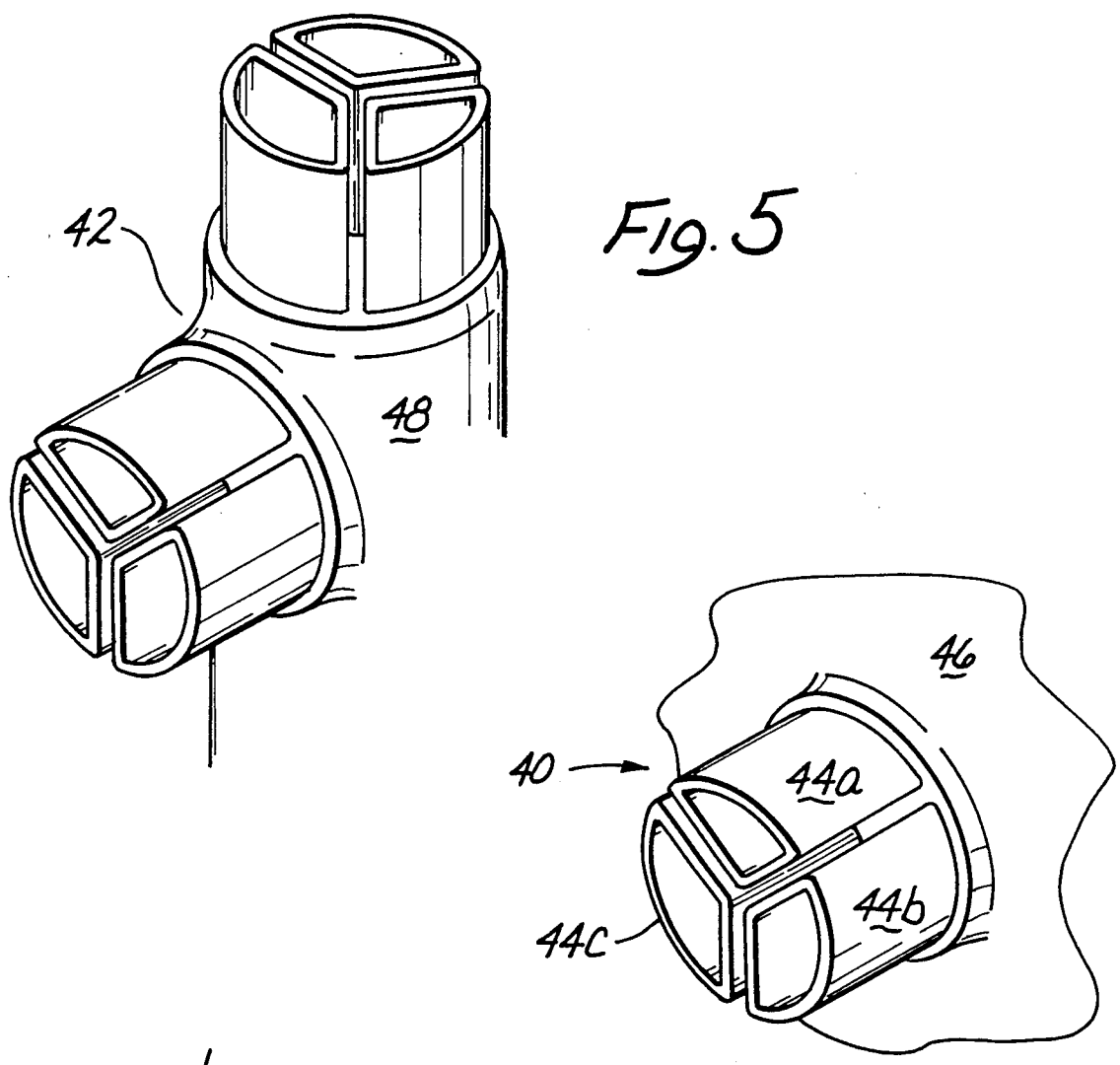
Fig. 5
Fig. 6
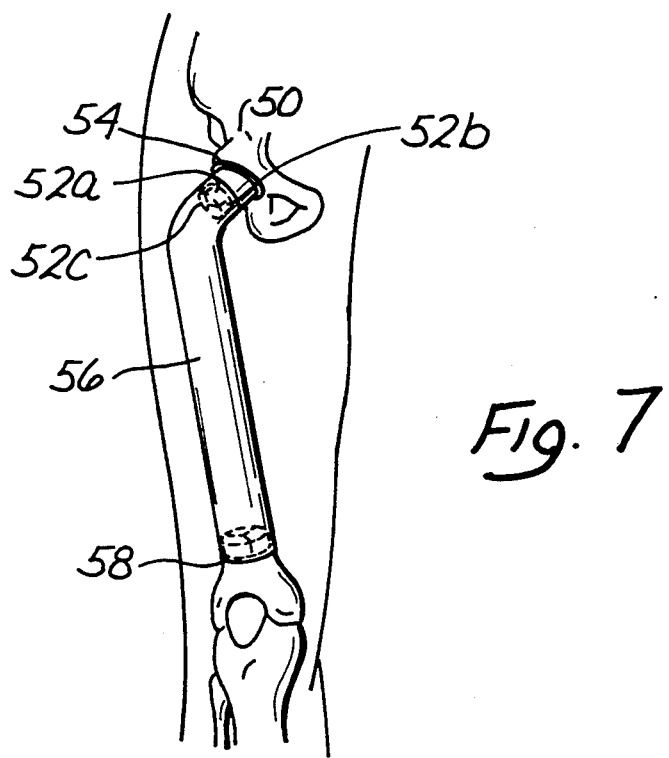
Fig. 7

HIGH STRENGTH, THIN-WALLED, PLASTIC TUBES AND CONNECTOR COMBINATION AND METHOD OF FABRICATION

FIELD OF THE INVENTION

This invention relates broadly to the field of structural elements, and particularly to tubular elements comprised of extrusions of short carbon fiber resins and connectors injection molded of similar resins.

BACKGROUND OF THE INVENTION

Considerable attention has been devoted by industry in general to utilizing recently developed high strength plastics, such as polyetheretherketone (PEEK), a short carbon-fiber resin with surface hardness and elongation percentage surpassing quality steel performance modulus, as a substitute for metals, such as steel and aluminium, in various parts and items produced by the aircraft/aerospace industry. While plastics composites have been recognized as utilizable to produce substitutes for metal parts, the manner in which such plastics have been employed has not been such as properly to utilize a potential of such recently developed short carbon fiber resins.

Thus, tubes employed in structural elements for bicycles, airframes and the like, generally have been fabricated by applying a malleable resin impregnated fabric in wires to a mandril or form for shaping. Such a process has been time consuming and has not produced the most effective structural elements which can be made of such short carbon fiber resins.

SUMMARY OF THE INVENTION

The present invention provides for the production of high aspect tubular elements and connectors for such elements by extruding a short carbon fiber resin, such as PEEK, into a tubular formed having a wall thickness of approximately 0.060", with an integrally cast interior matrix of similar walls or ribs extending from inside of the tubewall join to each other in the axis of the tube, with each wall being spaced equidistically from the other walls where they extend radially inwardly from the tube. The tubing may be sheathed in aluminium, such as aircraft grade cold-drawn seamless aluminium in variations in alloy from 5052 to 7075, and temper from T4 to t6.

For connecting the end of each tube to the end of an other tube, or to a wall, post, joint or some other fixture, a novel connector or anchoring means is provided. Such connector means may comprise a short tubular section injection molded or otherwise cast from a similar resin, but with a wall approximately twice as thick as the wall of the tube to be connected. The radially inner half of said section wall, carries such number of axial projections as equal the number of passageways defined by the matrix of inner walls in the tube. A cross-section of these extensions may be seen to provide a plurality of circular sectors spaced apart from each other by the thickness of the radial walls of the matrix in the tube with the diameter of the circle in which lie the outer walls of said sectors, being sufficiently smaller than the inside diameter of the tubular element to enable the extensions from the circular section to be pushed in into the tube when properly aligned so that the radial matrix walls may pass into the spacing between the adjacent sectors.

Where two tubular elements are to be joined, such projections may extend from each end of the tubular section of the connector. However, where a tubular element is to be connected to a joint, a wall or some other member, the latter desirably will have cast or molded into it a short cylindrical section with the sector extensions similarly formed, as described above, so that the end of the tubular element to be attached may be slipped over said sector projections to effect the desired joinder of the tubular element with the remainder of the structure carrying the tubular section and its projections. It would be possible, however, to eliminate the tubular section portion altogether from the member and instead, have the desired projections molded to extend directly form the member so that the tubular element when slipped over the projections would abut preferrably an annular area of the member.

Each connection may be secured against withdrawal of the projections by the application to the outside of at least a portion of each projection of a light coating of a structural aircraft adhesive (epoxy) such as DT 190 made and sold by the 3M Company.

While it is preferred to have the matrix of internal walls extruded with the extrusion of the tubular element, and as such, integrated with the inner wall of the tubular element; it would also be possible to extrude such matrix separately and the tubular element separately. The matrix could later be cut to the length of tubular element in which it is to be inserted, and then pushed into the latter, either with or without an application of the structural aircraft adhesive on the outer edges of the radial walls of the matrix to secure the matrix in one position within the tubular element.

It will be found that tubes so extruded with the matrix of internal walls will have a high degree of rigidity and strength, and when joined with either another tube or some structure having a type of connection means of the present invention, the strength of the tube will be further augmented at its point of joinder with the connection means.

Because of the light weight but high degree of strength and rigidity of the tube and its connection means, the present invention will have many uses, particularly as a substitute for metal in structures such as space frames and aerospace structures, sports equipment, walking aids, prosthetic devices, bone replacement elements, oil drilling equipment, scaffolding and temporary structures, drive shafts and other automotive structures.

DESCRIPTION OF THE DRAWINGS

In the accompanying drawings:

FIG. 1 is a perspective view of a portion of a bicycle frame having two interconnected tubes of the present invention.

FIG. 2 is an enlarged section taken along the line 2—2 of FIG. 1 looking in the direction of the arrows.

FIG. 3 is a section taken on the line 3—3 of FIG. 2.

FIG. 4 is an exploded and enlarged view of the connector and the ends of two tubular elements to be connected by the connector.

FIG. 5 is a perspective view of an angle juncture;

FIG. 6 is a perspective view of a wall terminal to which a tubular element has been attached;

FIG. 7 is a perspective view of a possible medical application of the invention.

DESCRIPTION OF THE PREFERRED EMBODIMENT

FIG. 1 of the drawing shows a portion of a bicycle frame 10 with a bar 12 which extends between, and is connected to the seat post 14 and the steering post 16. The bar 12 is comprised of two tubes 18 and 20, made and connected together in coaxial alignment by connector means 22 in accordance with the present invention.

The details of the structure of the tubes 18 and 20 and the connector 22, are shown in the enlarged views of FIGS. 2, 3 and 4. The tubes 18 and 20 are similar in all espects, except length. As previously mentioned, each tube 18, 20 may be an extrusion of PEEK or a similar resin with a short carbon fiber and desirably may be extruded to provide a thickness of the tube wall 24 of approximately 0.060". The tubes 18 and 20 are internally reinforced by a matrix 26 comprised in the illustrated example, of 3 walls or ribs 28a, 28b and 28c, each of which extends the full length of the tube 18 or 22, is integrally formed internally with the wall 24 and is directed radially-inwardly to the axis 30 of the tube 18 or 20, where it is integrally joined with the other similar walls as best shown in FIGS. 2 and 4. The three walls 28a, 28b and 28c in conjunction with the tube wall 24, thus define three passageways 32a, 32b and 32c, each of which in cross section is a circular sector, as best shown in FIG. 2. The walls 32a, 32b and 32c, thus formed with the tube wall 24, result in the formation of a rigid tube with even greater strength than that provided by the extruded PEEK material itself.

Connection of the tubes 18 and 20 may be effected by the connector 22. Although this connector 22 could be extruded and machined to its configuration hereafter described, it is preferably injection molded of the same PEEK or other similar resin. The connector 22 is formed with a short cylindrical section 34, desirably having a wall 35 which may be twice as thick as the walls 24 of the tubes 18 and 20. Extending from each end of the short cylindrical section 34 are a plurality of projections 36a, 36b and 36c, each of which in cross-section is also in the configuration of a circular sector, but sufficiently smaller than the passageways 32a, 32b and 32c to be insertable therein respectively in a close fit. In order to be so insertable, each of the projections 32a, 32b and 32c must be laterally spaced from its adjacent projections by a distance slightly greater than the thickness of the walls 28a, 28b and 28c respectively. Desirably the circular shoulder 38 formed at each end of the cylinder section 34 around the bases of the projections 36a, 36b and 36c, is of the same height as the thickness of the wall 24 of each tube 18 and 20. Thereby, when the ends of tubes 18 and 20 are brought into axial alignment with the ends of the connector 22 and the projections 36a, 36b and 36c are pushed into the passageways 32a, 32b and 32c respectively, the outside of the wall 35 of the connector will be flush with the outside of the wall 24 of each tube 18, 20, as best shown in FIG. 3. It may also be observed from FIG. 3 that while normally the greatest weakness in a connected tube occurs at its connected end, because of the manner in which the tubes 18, 20 are connected in the present invention, greater strength is actually imparted at the tube end connection.

If the projections 36a, 36b and 36c fit tightly in the passageways 32a, 32b and 32c respectively, and the tubes 18 and 20 are not be expected to be subjected to oppositely directed axial forces, as in the bar structure 12 shown in FIG. 1, it may not be necessary to apply any adhesive to the areas where the projections 32a, 32b, 32c contact the inside of the the wall 24 defining such passageways. However, ordinarily a suitable adhesive 37 should be applied, particularly when the tubes 18, 20 may be subjected to axial forces tending to pull each tube 18 and 20 in an axially opposite direction from the connector 22. The preferred type of adhesive 37 would be a structural aircraft adhesive which is an epoxy, such as DT 190 sold by the 3M Company of Minneapolis, Minn. A thin coating 37 of such adhesive may thus be applied about the rounded outside surfaces of the projections 36a, 36b and 36c, just prior to inserting them in the respective passageways 32a, 32b and 32c in the tubes 18, 20.

While tubes may be connected as shown in FIGS. 1 through 4 as heretofore discussed, it is also possible to provide one terminal 40 or a joint 42 of the type shown in FIGS. 5 and 6. In these embodiments provision is made for a similar joinder of a tube 18 to a terminal 40 having projections 44a, 44b, 44c similar to projections 36a, 36b 36c in the connector 22 shown in FIGS. 3 and 4. These projections may be integrally cast or injection molded with either an anchoring portion 46 of the terminal 40, or the remainder 48 of the joint 42 as shown in FIG. 6.

Because of the strength and light weight of the tubing, it may also have application as bone replacement as shown in FIG. 7. Where used with a plastic joint 50, the projections 52a, 52b, 52c as may be cast or injection molded either as a part of a joint 50 or with a connector end 54 of the type shown in FIGS. 4, 5 and 6, as illustrated in FIG. 7. Similarly at the opposite end of the bore replacement tube 56, a connector end 58 may be molded of cast to effect a connection.

From the foregoing it may be seen that tubing fabricated in accordance with the present invention may have many uses, and wide applications, particularly when employed in combinations with connectors or terminal ends having the projections insertable into the ends of the passageways in the tubing. The tubing itself desirably may be extruded, but the connectors, because of their slotting between the projections, desirably should be injection molded, although they could also be extruded and then machined to the configuration shown in FIG. 4, or to any required configuration.

I claim:

1. A high strength thin walled plastic tube and connector combination, said combination comprising:

A. a pair of thin walled tubular elements, each of said elements being comprised of a high strength linear aromatic polymer, said element having a predetermined external diameter, and a matrix of walls extending internally for the length of the element, each wall of the matrix extending radially inwardly from a predetermined axially extending line along the inside of the tubular element wall and joined with the other matrix walls along the element axis, thereby to provide internal support for the tubular element against bending, said matrix walls and the inside of the tube element wall defining a plurality of similar passageways within the tubular element; and B. connector means for said tubular element, said connector means also being formed of a similar high strength aromatic polymer to provide a short tubular section of the same predetermined external diameter as that of the tubular element, but said section having a thicker wall, said section further having a plurality of hollow projections corresponding in number to the number of passageways in the tubular element extending from each end of said section for a predetermined distance, each said projection conforming in its external shape and alignment with, and being of such size as to be insertable into and fit within the end of one of said passagways in one of said tubular elements, whereby said connector means, when brought into co-axial abutment with the end of each tubular element and with each of its projections coaligned with one of the passageways in said element, when each of said elements and said connector means are pushed together axially, all said projections are inserted into and slideably fitted within the correspondingly aligned passageways in the respective element to bring said short tubular section of the connector means into abutment with the ends of the tubular elements, thereby to connect both tubular elements through said connector means.

2. A high strength thin walled plastic tube and connector combination, said combination comprising:

A. a thin walled tubular element comprised of a high strength linear aromatic polymer, said element having a predetermined external diameter, and a matrix of walls extending internally for the length of the element, each wall of the matrix extending radially inwardly from a predetermined axially extending line along the inside of the tubular element wall and joined with the other matrix walls along the element axis, thereby to provide internal support for the tubular element against bending, said matrix walls and the inside of the tube element wall defining a plurality of similar passageways within the tubular element; and B. connector means for said tubular element, said connector means also being formed of a high strength aromatic polymer to provide a short tubular section of the same predetermined external diamter as that of the tubular element, but said section having a thicker wall, said section further having hollow projections extending from at least one end of said section about the axis thereof in such number as equals the number of said passageways in the tubular element, each of said projections in cross section being in the shape of a circular sector spaced from the other two sectors and from the sector axis by a slightly greater distance than the thickness of the matrix walls, and disposed in alignment parallel to the cylindrical section axis and alignable with the passageways in the tubular element, each said projection having an outer arcuate wall portion comprising an extension of the radially inner portion of the wall of the cylindrical section and a pair of radially inwardly directed walls extending from the extremities of said outer wall portion and joined at an angle, each said projection being of such size and dimension as to be insertable into one of said passageways, whereby said connector means, when brought into co-axial abutment with an end of said tubular element and with each of its projections coaligned with one of the passageways in said element, when said element and said connector means are pushed together axially, all said projections are inserted into and slideably fitted within the correspondingly aligned passageways to bring said short tubular section of the connector means into abutment with the end of the tubular element.

3. The combination as described in claim 1 wherein the end of the tubular section from which the hollow projections extend, when the latter are inserted into the passageways in a tubular element, the section end is joined flushly with the end of each tubular element.

4. In combination:

A. a thin walled tubular element comprised of a high strength linear aromatic polymer, said element having a predetermined external diameter, and a matrix of walls extending axially internally for the length of the element, each wall of the matrix extending radially inwardly from a predetermined axially extending line along the inside of the tubular element inner wall and joined with the other matrix walls along the element axis, thereby to provide internal support for the tubular element against bending, said matrix walls and the wall of the tubular element defining a plurality of similar passageways within the tubular element;

B. a member to which said tubular element is to be fixedly secured; and

C. means to secure said tubular element to said member, said means comprising a plurality of parallel projections extending from said member, each of said projections in cross-section comprising a circular sector, with the external walls of all said projections being encompassed by a common circle, said circle being slightly less in diameter than the diameter of the inside wall of the tubular element and each of said projections being spaced from each other and of such size and configuration as to be slideably insertable into one of said passageways in the tubular element, whereby when all said projections are so inserted into the passageways in said tubular element, the latter becomes fixedly secured to said member.

5. The combination as described in claim 4 wherein adhesive is applied to the outsides of said projections prior to their being inserted into the passageways.

6. The combination as described in claim 2 wherein the tubular element and connector means are so dimensioned that when brought together with the projections inserted in the passageways, the cylindrical section of the connector means and the wall of the tubular element are brought into flush abutment.

7. The combination as described in claim 2 wherein a thin aluminum sheath is placed over the outride of the tubular element.

8. The combination as described in claim 2 wherein a thin aluminum sheath is placed over the outside of the circular section of the connector means.

9. The combination as described in claim 2 wherein a thin aluminum sheath is placed over the outside of the tubular element and the circular section of the connector means.

10. The method of manufacturing the combination as described in claim 2 wherein the tubular element, including its matrix of walls is formed as a single extrusion of PEEK, and the connector means is injection molded of a similar aromatic polymer.

11. The method of manufacturing the combination as described in claim 2 wherein the tube portion of the tubular element is extruded separately from the matrix of walls which is also extruded, both of PEEK, and both the tubular element and matrix are cut to a desired length and the matrix is then inserted fully into the tubular element; and the connector means is injection molded of a similar aromatic polymer.

* * * * *